US009622954B2

(12) United States Patent
Kergosien

(10) Patent No.: US 9,622,954 B2
(45) Date of Patent: *Apr. 18, 2017

(54) COSMETIC COMPOSITION COMPRISING AN UREA OR AMIDE BASED ALPHA-ALKOXYSILANE

(71) Applicant: L'OREAL, Paris (FR)

(72) Inventor: Guillaume Kergosien, Chaville (FR)

(73) Assignee: L'OREAL, Paris (FR)

( * ) Notice: Subject to any disclaimer, the term of this patent is extended or adjusted under 35 U.S.C. 154(b) by 80 days.

This patent is subject to a terminal disclaimer.

(21) Appl. No.: 14/357,338

(22) PCT Filed: Nov. 9, 2012

(86) PCT No.: PCT/IB2012/056276
§ 371 (c)(1),
(2) Date: May 9, 2014

(87) PCT Pub. No.: WO2013/068966
PCT Pub. Date: May 16, 2013

(65) Prior Publication Data
US 2014/0328781 A1    Nov. 6, 2014

Related U.S. Application Data

(60) Provisional application No. 61/565,523, filed on Dec. 1, 2011.

(30) Foreign Application Priority Data

Nov. 9, 2011 (FR) ..................... 11 60225

(51) Int. Cl.
| | |
|---|---|
| A61K 8/58 | (2006.01) |
| A61Q 1/10 | (2006.01) |
| A61Q 3/02 | (2006.01) |
| A61Q 5/06 | (2006.01) |
| A61Q 19/00 | (2006.01) |
| A61K 8/04 | (2006.01) |
| A61Q 1/02 | (2006.01) |
| A61Q 1/06 | (2006.01) |
| A61Q 5/00 | (2006.01) |
| A61Q 19/08 | (2006.01) |

(52) U.S. Cl.
CPC ............. *A61K 8/585* (2013.01); *A61K 8/042* (2013.01); *A61Q 1/02* (2013.01); *A61Q 1/06* (2013.01); *A61Q 1/10* (2013.01); *A61Q 3/02* (2013.01); *A61Q 5/00* (2013.01); *A61Q 5/06* (2013.01); *A61Q 19/00* (2013.01); *A61Q 19/08* (2013.01); *A61K 2800/10* (2013.01); *A61K 2800/31* (2013.01)

(58) Field of Classification Search
CPC ... A61K 8/25; A61K 8/30; A61K 8/35; A61K 8/36; A61K 8/365; A61K 8/92
USPC ............. 424/400, 401, 70.11, 70.12, 70.121
See application file for complete search history.

(56) References Cited

U.S. PATENT DOCUMENTS 6,136,300 A * 10/2000 Ellingson ............. A61K 8/8152
                                                     424/401
6,352,699 B1   3/2002 Mondet et al.
(Continued)

FOREIGN PATENT DOCUMENTS

| EP | 1 717 240 | 11/2006 |
|---|---|---|
| WO | 98 44906 | 10/1998 |

(Continued)

OTHER PUBLICATIONS

Lukevits, et al., "Synthesis and Neurotropic Activity of Germatranylmethylamides and -Imides", 1998 Plenum Publishing Corporation, pp. 114-117, XP05503427, (Jan. 1988).
International Search Report Issued Sep. 11, 2013 in PCT/IB12/056276 Filed Nov. 9, 2012.
Written Opinion of the International Searching Authority Issued Sep. 11, 2013 in PCT/IB12/056276 Filed Nov. 9, 2012.
(Continued)

*Primary Examiner* — Micah-Paul Young
(74) *Attorney, Agent, or Firm* — Oblon, McClelland, Maier & Neustadt, L.L.P.

(57) ABSTRACT

The invention relates to a cosmetic composition, in particular a composition for making up and/or caring for keratin materials, preferably a nail makeup, comprising the compound of chemical formula (I) below: (I) in which: m represents an integer equal to 0 or 1; n represents an integer between 2 and 8; R1 represents a group ($C_1$-$C_{20}$)alkyl or an aryl group, or alternatively, when m is equal to 0, $R_1$ may also represent a carbonyl; R2 and R3 represent an ethoxy group or a group ($C_1$-$C_{20}$)alkyl, optionally substituted with an amino group; Y represents a polyurea or a polyurethane or alternatively a hydrocarbon-based group comprising from 2 to 100 carbon atoms. The invention also relates to a cosmetic process, in particular a makeup or hair shaping process, preferably a process for making up keratin materials, in particular the nails and/or the hair, characterized in that it comprises at least one step which consists in applying a cosmetic composition as above defined to keratin materials.

21 Claims, No Drawings

(56) References Cited

U.S. PATENT DOCUMENTS

| | | | |
|---|---|---|---|
| 2006/0111505 A1 | 5/2006 | Schindler et al. | |
| 2008/0269406 A1 | 10/2008 | Bachon et al. | |
| 2009/0075096 A1* | 3/2009 | Butikofer | C07F 7/1836 |
| | | | 428/447 |
| 2011/0301639 A1 | 12/2011 | Beckmann | |
| 2014/0343016 A1* | 11/2014 | Kergosien | A61Q 3/02 |
| | | | 514/63 |

FOREIGN PATENT DOCUMENTS

| | | |
|---|---|---|
| WO | 2010 008154 | 1/2010 |
| WO | 2011 150199 | 12/2011 |

OTHER PUBLICATIONS

French Search Report Issued Aug. 6, 2012 in FR 1160225 Filed Nov. 9, 2011.
French Written Opinion Issued Aug. 6, 2012 in FR116022 Filed Nov. 9, 2011 (with Machine Translation ).

\* cited by examiner

COSMETIC COMPOSITION COMPRISING AN UREA OR AMIDE BASED ALPHA-ALKOXYSILANE

A subject of the present invention is a cosmetic composition of sol/gel type for making up and/or caring for keratin materials.

The use of sol/gel techniques for the purposes of preparing cosmetic compositions is known per se. Such compositions form films after application to keratin materials. After drying, a hybrid material is in fact formed by polycondensation and crosslinking at the nanometric scale.

For example, patent application WO 98/44906 discloses a cosmetic or dermatological composition suitable for forming a coating on keratin materials via a reaction of sol/gel type obtained by mixing (A) at least one organometallic compound with (B) at least one functionalized organic polymer or at least one functionalized silicone polymer other than the first compound, and (C) an amount of water sufficient to hydrolyse the organometallic compound.

There is a need to provide compositions using sol/gel reactions that allow stability properties before they are applied to keratin materials in addition to good reactivity, and that also allow long remanence after application.

Rapid drying of the film or coating obtained is also sought.

Specifically, the coat of the composition deposited on the keratin materials may, if the reaction takes place slowly and if it does not dry quickly, prove to be tacky after its application and/or to be degraded on contact with foreign bodies, for instance a glass, a cigarette, an item of clothing or the skin, which will be an inconvenience to users.

In addition, properties of remanence on washing with water and with detergents are sought.

Finally, it is sought to obtain a strong, adherent film.

The inventors have found that such advantages may be obtained by using alpha-alkoxysilanes comprising, in the position alpha to the alkoxysilane, an amide or urea group.

The presence of an electron-donating group alpha to the silicon allows improved reactivity with atmospheric moisture, and within a short time, in comparison with alkoxysilanes not comprising such an electron-donating group.

Compositions based on alpha-alkoxysilanes comprising an amide or urea group alpha to the alkoxysilane have already been described, especially in patent application US 2008/0 269 406. However, the nitrogen atoms of the said amide and urea functions of the said application are free, in contrast with those of the present invention.

Thus, the subject of the present invention is a cosmetic composition, in particular a composition for making up and/or caring for keratin materials, preferably a nail makeup, comprising the compound of chemical formula (I) below:

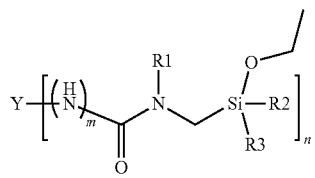

(I)

in which:
m represents an integer equal to 0 or 1;
n represents an integer between 1 and 8;

R1 represents a group $(C_1-C_{20})$alkyl or an aryl group, or alternatively, when m is equal to 0, $R_1$ may also represent a carbonyl;

R2 and R3 represent an ethoxy group or a group $(C_1-C_{20})$ alkyl, optionally substituted with an amino group;

Y represents a polyurea or a polyurethane or alternatively a hydrocarbon-based group comprising from 2 to 100 carbon atoms, the said hydrocarbon-based group possibly being a linear or branched monovalent or multivalent, optionally unsaturated group, optionally bearing one or more aromatic or non-aromatic cyclic groups, the said carbon atoms possibly being substituted with one or more groups chosen from an ethoxy group and an amino group, one or more of the said carbon atoms possibly being independently replaced with
a nitrogen atom,
a group —SiO—,
a polydimethylsiloxane group,

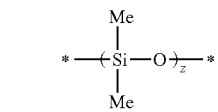

in which z may be between 1 and 20, or
a carbonyl group,
the said hydrocarbon-based group possibly forming with the group R1 one or more rings, depending on its valency.

According to one preferred embodiment, a subject of the present invention is a cosmetic composition as described above in which n represents an integer between 2 and 8.

In the context of the present invention, the term:
"keratin materials" denotes the skin, the lips and/or integuments such as the nails and keratin fibres, for example the eyelashes, the eyebrows and the hair;
"alkoxysilane" denotes a compound comprising at least one silicon atom bearing at least one alkoxy group;
"property of stability before application" denotes the ability to remain in liquid form, i.e. not to gel, before application to the keratin materials;
"hydrocarbon-based group" denotes a linear or branched monovalent or multivalent, optionally unsaturated group containing carbon and hydrogen atoms, optionally bearing one or more aromatic or non-aromatic cyclic groups, bearing from 2 to 100 carbon atoms;
"$(C_1-C_{20})$alkyl" denotes a linear, branched or cyclic, saturated or unsaturated hydrocarbon-based group comprising from 1 to 20 carbon atoms. Mention may be made in particular of cyclohexyl and methyl groups;
"aryl" denotes an aromatic bearing from 5 to 14 carbon atoms. Mention may in particular be made of the benzyl group or the phenyl group;
"carbonyl" denotes the group having the following formula:

"amino" denotes the group having the following formula:
—NH$_2$

"polyurea" denotes a group having the following formula:

$$*-R'-\left[\underset{H}{N}-\underset{\underset{R''}{|}}{C(O)}-\underset{\underset{R''}{|}}{N}-R-N-C(O)-\underset{H}{N}-R'-\right]_n*$$

in which R represents a linear, branched or cyclic, saturated or unsaturated hydrocarbon-based group, comprising from 1 to 50 and especially from 1 to 20 carbon atoms, R' represents a linear, branched or cyclic, saturated or unsaturated hydrocarbon-based group, comprising from 1 to 50 and especially from 1 to 20 carbon atoms, R" represents a hydrogen atom or a linear, branched or cyclic, saturated or unsaturated hydrocarbon-based group comprising from 1 to 20 carbon atoms, and n represents an integer between 1 and 10;

"polyurethane" denotes a group having the following formula:

$$*-R'-\left[NH-C(O)-O-R-O-C(O)-NH-R'-\right]_n*$$

in which R represents a polyether group, a polyester group or a linear, branched or cyclic, saturated or unsaturated hydrocarbon-based group, comprising from 1 to 50 and especially from 1 to 20 carbon atoms, R' represents a linear, branched or cyclic, saturated or unsaturated hydrocarbon-based group, comprising from 1 to 50 and especially from 1 to 20 carbon atoms, and n represents an integer between 1 and 10;

"($C_1$-$C_3$)aminoalkyl" denotes a linear, branched or cyclic, saturated or unsaturated hydrocarbon-based group comprising from 1 to 3 carbon atoms, one of the carbon atoms being substituted with a group —$NH_2$;

"($C_1$-$C_{20}$)alkylene" denotes a linear or branched saturated divalent alkyl group comprising from 1 to 20 carbon atoms;

"between" denotes inclusively between.

The compound of formula (I) according to the invention may be obtained by reaction between an alpha-amino ethoxysilane and:
an isocyanate (when n is equal to 1) or a polyisocyanate when m is equal to 1,
an acid (when n is equal to 1), an anhydride, a polyacid, an ester (when n is equal to 1) or a polyester when m is equal to 0.

The starting materials are either commercially available or obtained according to methods known to those skilled in the art.

As regards the alpha-amino ethoxysilanes, examples that may be mentioned include (N-cyclohexylaminomethyl)triethoxysilane sold by Gelest under the name SIC2464.2 and (N-cyclohexylaminomethyl)methyldiethoxysilane sold by Aber under the name AB152160.

As regards the isocyanates or polyisocyanates, examples that may be mentioned include isophorone diisocyanate sold by Evonik under the name Vestanat® IPDI or the equimolar mixture of 2,2,4-trimethylhexamethylene diisocyanate and of 2,4,4-trimethylhexamethylene diisocyanate sold by Evonik under the name Vestanat® TMDI.

The invention also relates to a cosmetic process, in particular a makeup or hair shaping process, preferably a process for making up keratin materials, in particular the nails and/or the hair, comprising at least one step which consists in applying the cosmetic composition according to the invention to keratin materials.

A cosmetic composition according to the present invention is liquid.

In the context of the present invention, the term "liquid composition" means a composition which has a particular viscosity at room temperature, i.e. at 20° C.

More specifically, a liquid composition has, at 20° C., a viscosity ranging from 0.001 to 20 Pa/s, preferably from 0.01 to 10 Pa/s and even more preferably from 0.1 to 2 Pa/s.

The viscosity measurement may be carried out at 20° C. using a Rheomat RM180 viscometer equipped with a No. 4 rotor, the measurement being performed after 10 minutes of rotation of the rotor in the composition (after which time stabilization of the viscosity and of the spin speed are observed), at a shear rate of 200 $s^{-1}$.

Alpha-Alkoxysilanes

According to one of its aspects, a subject of the present invention is a cosmetic composition comprising the compound of chemical formula (I) for which Y represents a polyurea, a polyurethane or a group Y chosen from one of the groups of formulae (II) to (XXIII) below when m is equal to 0 or 1 and from one of the groups of formulae (XXIV) to (XXVII) below when m is equal to 0 and R1 represents a carbonyl group:

(II)

in which:
x being between 1 and 10;
when m is equal to 1, then x is preferably equal to 3;
when m is equal to 0, then x is between 2 and 4;

(III)

(IV)

(V)

(VI)

(VII)

-continued (VIII)
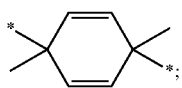

(IX)

(X)
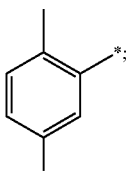

(XI)
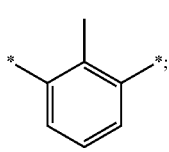

(XII)
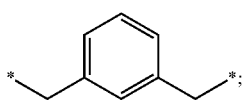

(XIII)
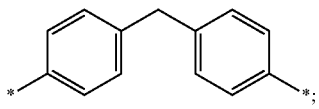

(XIV)
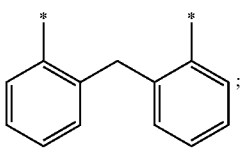

(XV)
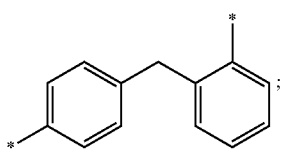

(XVI)
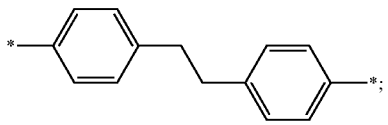

(XVII)
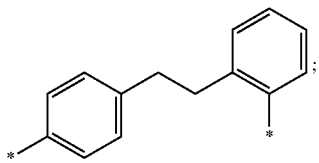

(XVIII)
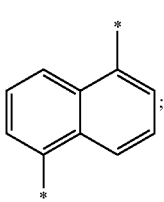

(XIX)
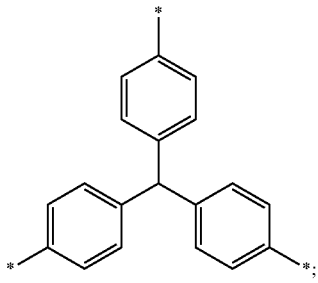

(XX)
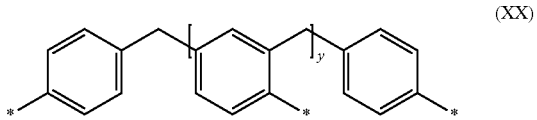

in which y is between 1 and 6 and, preferably, y is between 1 and 4;

(XXI)
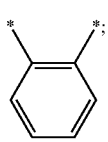

(XXII)

(XXIII)

in which:

R7 represents a group $(C_1-C_{20})$alkyl, an aryl group or a group $(C_1-C_{20})$alkylene linked to R1, preferably a group $(C_1-C_{20})$alkylene linked to R1;

R8 and R9 independently represent an ethoxy group or a group $(C_1-C_{20})$alkyl optionally substituted with an amino group, preferably a methyl or a group $(C_1-C_3)$aminoalkyl;

(XXIV)

in which:

$X_1$ and $X_2$ independently represent a covalent bond linked to the group R1, the said group R1 representing a carbonyl;

A represents a group $(C_1-C_{20})$alkylene, a carbonyl group or a polydimethylsiloxane having the following formula

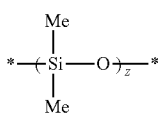

in which z may be between 1 and 20;

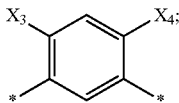

in which $X_3$ and $X_4$ independently represent a covalent bond linked to the group R1, the said group R1 representing a carbonyl;

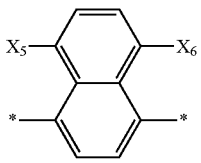

in which $X_5$ and $X_6$ independently represent a covalent bond linked to the group R1, the said group R1 representing a carbonyl;

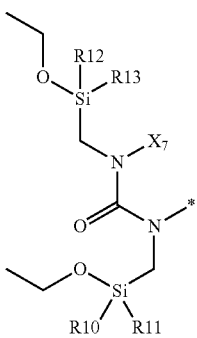

in which:

$X_7$ represents a covalent bond linked to the group R1, the said group R1 representing a carbonyl;

R10, R11, R12 and R13 independently represent an ethoxy group or a group ($C_1$-$C_{20}$)alkyl optionally substituted with an amino group, preferably a methyl or a group ($C_1$-$C_3$)aminoalkyl.

According to one particular embodiment, a subject of the present invention is a cosmetic composition comprising the compound of chemical formula (I) for which Y has a molar mass of less than 3000 g/mol, preferably less than 1500 g/mol and preferentially less than 1000 g/mol.

According to one particular embodiment, a subject of the present invention is a cosmetic composition comprising the compound of chemical formula (I) for which n is between 2 and 4, and preferably n is equal to 2.

According to one particular embodiment, a subject of the present invention is a cosmetic composition comprising the compound of chemical formula (I) for which R1 represents a cyclohexyl or phenyl group, and preferably R1 represents a cyclohexyl group.

According to one particular embodiment, a subject of the present invention is a cosmetic composition comprising the compound of chemical formula (I) for which m is equal to 0 and R1 represents a carbonyl group, the said group R1 moreover being linked via a covalent bond to one of the atoms of the group Y.

According to one particular embodiment, a subject of the present invention is a cosmetic composition comprising the compound of chemical formula (I) for which R2 and R3 independently represent a methyl group, a group ($C_1$-$C_3$) aminoalkyl or an ethoxy group.

According to one particular embodiment, a subject of the present invention is a cosmetic composition comprising the compound of chemical formula (I) for which m is equal to 1.

According to one particular embodiment, a subject of the present invention is a cosmetic composition comprising the compound of chemical formula (I) for which Y is a hydrocarbon-based group as defined above, comprising only carbon and hydrogen atoms.

According to one particular aspect of this embodiment, a subject of the present invention is a cosmetic composition comprising the compound of chemical formula (I) for which Y is a saturated hydrocarbon-based group comprising only carbon and hydrogen atoms, in particular represented by formulae (II) to (VII) as defined previously.

Still according to this same embodiment, the present invention consists of a cosmetic composition comprising the compound of chemical formula (I) for which Y is represented by formula (III), (IV) or (V) as defined previously.

According to one preferred embodiment, a subject of the present invention is a cosmetic composition comprising the compound of chemical formula (I) in a content of greater than or equal to 20% by weight and preferably greater than 50% by weight relative to the total weight of the composition.

Composition

The composition according to the invention is preferably anhydrous.

The term "anhydrous" refers to a composition comprising a content of less than or equal to 0.5% by weight of water relative to the total weight of the composition. The term "anhydrous" especially means that water is preferably not deliberately added to the compositions, but may be present in trace amount in the various compounds used in the compositions.

According to one particular embodiment, the composition according to the invention has a solids content of greater than or equal to 50% and preferably greater than 70%.

For the purposes of the present invention, the term "solids content" denotes the content of non-volatile matter.

The solids content (abbreviated as SC) of a composition according to the invention is measured using a "Halogen Moisture Analyzer HR83" commercial halogen desiccator from Mettler Toledo. The measurement is performed on the basis of the weight loss of a sample dried by halogen heating, and thus represents the percentage of residual matter once the water and the volatile matter have evaporated off.

This technique is fully described in the machine documentation supplied by Mettler Toledo.

The measuring protocol is as follows:

Approximately 2 g of the composition, referred to hereinbelow as the sample, are spread out on a metal crucible, which is placed in the halogen desiccator mentioned above. The sample is then subjected to a temperature of 120° C. for 1 hour. The wet mass of the sample, corresponding to its initial mass, and the dry mass of the sample, corresponding to its mass after halogen heating, are measured using a precision balance.

The values measured by means of the protocol described above may differ from the corresponding theoretical values by plus or minus 1%.

The solids content is calculated in the following manner:

Solids content (expressed as weight percentage)= 100×(dry mass/wet mass).

Other Alkoxysilane Compound

According to one particular embodiment, the composition according to the present invention also comprises at least one other compound comprising at least one alkoxysilane group.

The term "compound comprising at least one alkoxysilane group" preferably denotes a compound of formula $Si(OR^2)_4$ or of formula $R^1_xSi(OR^2)_{(4-x)}$ or of formula $[R^1_y(OR^2)_z SiO_{((4-y-z)/2)}]_n$ in which:
  $R^1$ represents, independently, a nucleophilic group other than a silanol, or a group $(C_1-C_{20})$alkyl, optionally substituted with at least one nucleophilic group other than a silanol,
  $R^2$ represents, independently, a hydrogen atom or a group $(C_1-C_{10})$alkyl,
  x represents 1 or 2,
  y represents, independently, 1 or 2,
  z represents, independently, 0, 1 or 2,
  the sum of y and z being less than or equal to 3,
  and n represents an integer between 2 and 1000.

Polar Volatile Solvent

According to one particular embodiment, the composition according to the present invention also comprises at least one polar volatile solvent.

The term "polar volatile solvent" denotes, in the present invention, a compound which is liquid at ambient temperature, which comprises at least one polar group such as a hydroxyl, ester, ketone, ether or aldehyde group, and which has a vapour pressure greater than 1 mbar at 20° C.

Among the polar volatile solvents that may be used in the compositions in accordance with the invention, mention may be made especially of lower monoalcohols containing from 1 to 5 carbon atoms such as ethanol and isopropanol, $C_3$-$C_4$ ketones, $C_2$-$C_4$ aldehydes and $C_2$-$C_4$ short-chain esters, and mixtures thereof. Preferably, the polar volatile solvents are chosen from $C_3$-$C_4$ ketones, preferentially acetone, and $C_2$-$C_4$ short-chain esters, preferentially ethyl acetate, and mixtures thereof.

Film-Forming Polymer

According to one particular embodiment, the composition according to the invention may also comprise at least one film-forming polymer. In particular, when the composition according to the present invention is in the form of a nail varnish, such a film-forming polymer may advantageously be present in the composition.

For the purposes of the present invention, the term "film-forming polymer" denotes a polymer that is capable, by itself or in the presence of an auxiliary film-forming agent, of forming an isolable and especially continuous and adherent film, on a support. This support may especially be the nails.

A single film-forming polymer or a mixture of film-forming polymers may be used in the composition.

This film-forming polymer may be chosen from the group formed by synthetic polymers of radical type or of polycondensate type, and polymers of natural origin, and mixtures thereof.

According to the invention, film-forming polymers that are soluble or dispersible in an organic solvent may be used.

A film-forming polymer that is suitable for use in the invention may be chosen in particular from:
  polysaccharides. Among the polysaccharides that are suitable for use in the invention, examples that may be mentioned include cellulose esters and ethers, such as nitrocellulose, cellulose acetate, cellulose acetobutyrate, cellulose acetopropionate and ethylcellulose, or alternatively optionally modified guar gum, such as ethylguar;
  synthetic polymers such as polyurethanes, acrylic polymers, vinyl polymers, polyvinyl butyrals, alkyd resins and ketone/aldehyde resins, resins derived from aldehyde condensation products, such as arylsulfonamide-formaldehyde resins, for instance toluenesulfonamide-formaldehyde resin, arylsulfonamide-epoxy resins or ethyl tosylamide resins;
  polymers of natural origin, such as plant resins, such as dammar resins, elemi gums, copal resins, and benzoin;
  gums such as shellac, sandarac gum and gum mastic.

Use may in particular be made, as film-forming polymers, of the toluenesulfonamide/formaldehyde resins Ketjentflex MS80 from Akzo or Santolite MHP or Santolite MS 80 from Faconnier or Resimpol 80 from Pan Americana, the alkyd resin Beckosol ODE 230-70-E from Dainippon, the acrylic resin Acryloid B66 from Röhm & Haas, the polyurethane resin Trixene PR 4127 from Baxenden or the acetophenone/formaldehyde resin sold under the reference Synthetic Resin SK by Degussa.

According to one particular embodiment, the film-forming polymer is chosen from polysaccharides or polysaccharide derivatives, preferably from nitrocellulose, and cellulose ethers and esters.

For example, the content of film-forming polymer may range from 0.1% to 30% by weight, especially from 0.5% to 20% by weight and in particular from 1% to 10% by weight relative to the total weight of the composition.

According to one particular embodiment, the composition according to the invention comprises as film-forming polymer at least cellulose derivatives, polyesters or polyurethanes.

Plasticizer

According to one particular embodiment, the composition according to the invention comprises at least one plasticizer.

In particular, mention may be made, alone or as mixtures, of plasticizers such as:
  glycols containing from 2 to 8 carbon atoms such as glycerol, propylene glycol, 1,3-butylene glycol and dipropylene glycol,
  glycol derivatives such as diethylene glycol ethyl ether, diethylene glycol methyl ether, diethylene glycol butyl ether or diethylene glycol hexyl ether, ethylene glycol ethyl ether, ethylene glycol butyl ether and ethylene glycol hexyl ether,
  glycol esters,
  propylene glycol derivatives and in particular propylene glycol phenyl ether, propylene glycol diacetate, dipropylene glycol butyl ether, tripropylene glycol butyl ether, propylene glycol methyl ether, dipropylene glycol ethyl ether, tripropylene glycol methyl ether, diethylene glycol methyl ether and propylene glycol butyl ether, fatty alcohols that are liquid at ambient temperature, with a branched and/or unsaturated carbon-based chain containing from 12 to 26 carbon atoms, for instance 2-octyldodecanol, isostearyl alcohol, oleyl alcohol, 2-hexyldecanol, 2-butyloctanol and 2-undecylpentadecanol, higher fatty acids such as oleic acid, linoleic acid or linolenic acid, and mixtures thereof, esters of acids, in particular carboxylic acids, such as the monoesters of formula $R_1COOR_2$ in which $R_1$ represents the residue of a linear or branched acid comprising from 1 to 40 carbon atoms and $R_2$ represents a hydrocarbon-based chain, which is in particular branched, containing from 1 to 40 carbon atoms, provided that $R_1+R_2>10$, triglycerides consisting of fatty acid esters glycerol, the fatty acids of which can have varied chain lengths from $C_4$ to $C_{24}$, citrates, in particular triethyl citrate, tributyl citrate, triethyl acetylcitrate, tributyl acetylcitrate, 2-triethylhexyl acetylcitrate; phthalates, in particular diethyl phthalate, dibutyl phthalate, dioctyl phthalate, dipentyl phthalate, dimethoxyethyl phthalate; trimellitates such as, in particular, tris(2-ethylhexyl)trimellitate, L7,9-trimellitate, L8,10-trimellitate; phosphates, in particular tricresyl phosphate, tributyl phosphate, triphenyl phosphate, tributoxyethyl phosphate; tartrates, in particular dibutyl tartrate; adipates, such as, in particular, diethyl adipate and diisobutyl adipate; carbonates; sebacates; benzyl benzoate, butyl acetylricinoleate, glyceryl acetylricinoleate, butyl glycolate, glyceryl triacetate, plasticizers of polyester type, camphor, N-ethyl-o,p-toluenesulfonamide, oxyethylenated derivatives such as oxyethylenated oils, in particular vegetable oils such as castor oil, linear or branched hydrocarbons of mineral or synthetic origin, such as petroleum jelly, polydecenes, hydrogenated polyisobutene such as Parleam®, and squalane, and mixtures thereof, and in particular hydrogenated polyisobutene, silicone oils. The silicone oils that may be used in the composition may be non-volatile polydimethylsiloxanes (PDMSs), polydimethylsiloxanes comprising alkyl or alkoxy groups that are pendent and/or at the end of a silicone chain, these groups each containing from 2 to 24 carbon atoms, phenyl silicones, for instance phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates, and dimethicones or phenyl trimethicones with a viscosity of less than or equal to 100 cSt, and mixtures thereof, and mixtures thereof.

The type and amount of plasticizer may be chosen by a person skilled in the art on the basis of his general knowledge.

For example, the plasticizer content may range from 0.01% to 10% and in particular from 1% to 5% by weight relative to the total weight of the composition.

According to one particular embodiment, the composition according to the invention comprises as plasticizer at least one fatty alcohol, or a carboxylic acid ester or polyester.

Wax(es)

The composition according to the invention preferably comprises at least one wax.

The wax(es) under consideration in the context of the present invention are generally a lipophilic compound that is solid at room temperature (25° C.), with a solid/liquid reversible change of state, having a melting point of greater than or equal to 30° C., which may be up to 200° C. and in particular up to 120° C.

In particular, the waxes that are suitable for the invention may have a melting point of greater than or equal to 45° C. and in particular of greater than or equal to 55° C.

For the purposes of the invention, the melting point corresponds to the temperature of the most endothermic peak observed on thermal analysis (DSC) as described in standard ISO 11357-3; 1999. The melting point of the wax may be measured using a differential scanning calorimeter (DSC), for example the calorimeter sold under the name DSC Q2000 by the company TA Instruments.

Preferably, the waxes have a heat of fusion ΔHf of greater than or equal to 70 J/g.

Preferably, the waxes comprise at least one crystallizable part, which is visible by X-ray observation.

The measuring protocol is as follows:

A sample of 5 mg of wax placed in a crucible is subjected to a first temperature rise ranging from −20° C. to 120° C., at a heating rate of 10° C./minute, is then cooled from 120° C. to −20° C. at a cooling rate of 10° C./minute and is finally subjected to a second temperature rise ranging from −20° C. to 120° C. at a heating rate of 5° C./minute. During the second temperature rise, the following parameters are measured:

the melting point ($T_f$) of the wax, as mentioned previously corresponding to the temperature of the most endothermic peak of the melting curve observed, representing the variation of the difference in power absorbed as a function of the temperature, ΔHf: the heat of fusion of the wax, corresponding to the integral entire melting curve obtained. This heat of fusion of the wax is the amount of energy required to make the compound change from the solid state to the liquid state. It is expressed in J/g.

The waxes that may be used in the composition according to the invention are chosen from waxes that are solid at room temperature, of animal, plant, mineral or synthetic origin, and mixtures thereof.

As illustrations of waxes that are suitable for the invention, mention may be made especially of hydrocarbon-based waxes, for instance beeswax, lanolin wax, Chinese insect waxes, rice bran wax, carnauba wax, candelilla wax, ouricury wax, esparto grass wax, berry wax, shellac wax, Japan wax and sumach wax; montan wax, orange wax and lemon wax, microcrystalline waxes, paraffins and ozokerite; polyethylene waxes, the waxes obtained by Fischer-Tropsch synthesis and waxy copolymers, and also esters thereof.

Mention may also be made of waxes obtained by catalytic hydrogenation of animal or plant oils containing linear or branched $C_8$-$C_{32}$ fatty chains. Among these, mention may be made especially of isomerized jojoba oil such as the trans-isomerized partially hydrogenated jojoba oil manufactured or sold by the company Desert Whale under the trade reference Iso-Jojoba-50®, hydrogenated sunflower oil, hydrogenated castor oil, hydrogenated coconut oil, hydrogenated lanolin oil, and the bis(1,1,1-trimethylolpropane) tetrastearate sold under the name Hest 2T-4S® by the company Heterene.

Mention may also be made of silicone waxes ($C_{30-45}$ alkyl dimethicone) and fluoro waxes.

The waxes obtained by hydrogenation of castor oil esterified with cetyl alcohol, sold under the names Phytowax ricin 16L64® and 22L73® by the company Sophim, may also be used. Such waxes are described in Application FR-A-2 792 190.

A wax that may be used is a $C_{20}$-$C_{40}$ alkyl (hydroxystearyloxy)stearate (the alkyl group containing from 20 to 40 carbon atoms), alone or as a mixture.

Such a wax is especially sold under the names Kester Wax K 82 P®, Hydroxypolyester K 82 P® and Kester Wax K 80 P® by the company Koster Keunen.

As microwaxes that may be used, mention may be made especially of carnauba microwaxes, such as the product sold under the name MicroCare 350® by the company Micro Powders, synthetic microwaxes, such as the product sold under the name MicroEase 114S® by the company Micro Powders, microwaxes consisting of a mixture of carnauba wax and polyethylene wax, such as the products sold under the names Micro Care 300® and 310® by the company Micro Powders, microwaxes consisting of a mixture of carnauba wax and of synthetic wax, such as the product sold under the name Micro Care 325® by the company Micro Powders, polyethylene microwaxes, such as the products sold under the names Micropoly 200®, 220®, 220L® and 2505® by the company Micro Powders, and polytetrafluoroethylene microwaxes, such as the products sold under the names Microslip 519® and 519 L® by the company Micro Powders.

Preferably, the composition according to the invention may comprise at least one hydrocarbon-based wax, preferably chosen from polyethylene waxes, microcrystalline waxes and ozokerite, and mixtures thereof.

Preferably, the first composition according to the invention comprises at least one polyethylene wax.

Preferably, the composition according to the invention comprises a content of wax(es) ranging from 0.1% to 40% by weight relative to the total weight of the composition; it may in particular contain from 0.5% to 20% and more particularly from 1% to 10% thereof.

Pasty Fatty Substances

The composition according to the invention may also comprise at least one pasty fatty substance.

For the purposes of the present invention, the term "pasty fatty substance" means a lipophilic fatty compound with a reversible solid/liquid change of state, comprising at a temperature of 23° C. a liquid fraction and a solid fraction.

In other words, the starting melting point of the pasty compound can be less than 23° C. The liquid fraction of the pasty compound measured at 23° C. can represent 9% to 97% by weight of the compound. This liquid fraction at 23° C. preferably represents between 15% and 85% and more preferably between 40% and 85% by weight.

Preferably, the pasty fatty substances have an end melting point of less than 60° C.

Preferably, the pasty fatty substances have a hardness of less than or equal to 6 MPa.

Preferably, the pasty fatty substances have, in the solid state, an anisotropic crystal organization, which is visible by X-ray observation.

For the purpose of the invention, the melting point corresponds to the temperature of the most endothermic peak observed on thermal analysis (DSC) as described in Standard ISO 11357-3; 1999. The melting point of a pasty substance or of a wax may be measured using a differential scanning calorimeter (DSC), for example the calorimeter sold under the name DSC Q2000 by the company TA Instruments.

As regards the measurement of the melting point and the determination of the end melting point, the sample preparation and measurement protocols are as follows:

A sample of 5 mg of pasty fatty substance, preheated to 80° C. and withdrawn with magnetic stirring using a spatula that is also heated, is placed in a hermetic aluminium capsule, or a crucible. Two tests are performed to ensure the reproducibility of the results.

The measurements are performed on the abovementioned calorimeter. The oven is flushed with nitrogen. Cooling is performed by an RCS 90 heat exchanger. The sample is then subjected to the following protocol: it is first placed at a temperature of 20° C., and then subjected to a first temperature rise passing from 20° C. to 80° C., at a heating rate of 5° C./minute, then is cooled from 80° C. to −80° C. at a cooling rate of 5° C./minute and finally subjected to a second temperature rise passing from −80° C. to 80° C. at a heating rate of 5° C./minute. During the second temperature rise, the variation in the difference between the power absorbed by the empty crucible and the crucible containing the sample of paste or wax as a function of the temperature is measured. The melting point of the compound is the value of the temperature corresponding to the top of the peak of the curve representing the variation in the difference in power absorbed as a function of the temperature.

The end melting point corresponds to the temperature at which 95% of the sample has melted.

The liquid fraction by weight of the pasty compound at 23° C. is equal to the ratio of the heat of fusion consumed at 23° C. to the heat of fusion of the pasty compound.

The heat of fusion of the pasty compound is the heat consumed by the compound in order to pass from the solid state to the liquid state. The pasty compound is said to be in the solid state when all of its mass is in crystalline solid form. The pasty compound is said to be in the liquid state when all of its mass is in liquid form.

The heat of fusion of the pasty compound is equal to the integral of the entire melting curve obtained using the abovementioned calorimeter, with a temperature rise of 5 or 10° C./minute, according to standard ISO 11357-3:1999. The heat of fusion of the pasty compound is the amount of energy required to make the compound change from the solid state to the liquid state. It is expressed in J/g.

The enthalpy of fusion consumed at 23° C. is the amount of energy absorbed by the sample to change from the solid state to the state that it has at 23° C., composed of a liquid fraction and a solid fraction.

The liquid fraction of the pasty compound measured at 32° C. preferably represents from 30% to 100% by weight of the compound, preferably from 50% to 100%, more preferably from 60% to 100% by weight of the compound. When the liquid fraction of the pasty compound measured at 32° C. is equal to 100%, the temperature of the end of the melting range of the pasty compound is less than or equal to 32° C.

The liquid fraction of the pasty compound measured at 32° C. is equal to the ratio of the heat of fusion consumed at 32° C. to the heat of fusion of the pasty compound. The enthalpy of fusion consumed at 32° C. is calculated in the same way as the enthalpy of fusion consumed at 23° C.

As regards the measurement of the hardness, the sample preparation and measurement protocols are as follows:

The pasty fatty substance is placed in a mould 75 mm in diameter, which is filled to about 75% of its height. In order to overcome the thermal history and to control the crystallization, the mould is placed in a Vötsch VC 0018 programmable oven, where it is first placed at a temperature of 80°

C. for 60 minutes, then cooled from 80° C. to 0° C. at a cooling rate of 5° C./minute, and then left at the stabilized temperature of 0° C. for 60 minutes, and then subjected to a temperature rise ranging from 0° C. to 20° C. at a heating rate of 5° C./minute, and then left at the stabilized temperature of 20° C. for 180 minutes.

The compression force measurement is taken using a TA/TX2i texturometer from Swantech. The spindle used is chosen according to the texture:
- cylindrical steel spindle 2 mm in diameter for very rigid starting materials;
- cylindrical steel spindle 12 mm in diameter for sparingly rigid starting materials.

The measurement comprises three steps: a first step after automatic detection of the surface of the sample, where the spindle moves at a measuring speed of 0.1 mm/s, and penetrates into the pasty fatty substance to a penetration depth of 0.3 mm, the software notes the maximum force value reached; a second "relaxation" step where the spindle remains at this position for one second and the force is noted after 1 second of relaxation; finally, a third "withdrawal" step in which the spindle returns to its initial position at a speed of 1 mm/s, and the probe withdrawal energy (negative force) is noted.

The hardness value measured during the first step corresponds to the maximum compression force measured in newtons divided by the area of the texturometer cylinder expressed in mm$^2$ in contact with the pasty fatty substance. The hardness value obtained is expressed in megapascals or MPa.

The pasty fatty compound may preferably be chosen from synthetic compounds and compounds of plant origin. A pasty fatty substance may be obtained by synthesis from starting materials of plant origin.

The pasty fatty substance is advantageously chosen from:
- lanolin and derivatives thereof, such as lanolin alcohol, oxyethylenated lanolins, acetylated lanolin, lanolin esters such as isopropyl lanolate, and oxypropylenated lanolins,
- polymeric or non-polymeric silicone compounds, for instance polydimethylsiloxanes of high molecular masses, polydimethylsiloxanes containing side chains of the alkyl or alkoxy type containing from 8 to 24 carbon atoms, especially stearyl dimethicones,
- polymeric or non-polymeric fluoro compounds,
- vinyl polymers, especially:
- olefin homopolymers,
- olefin copolymers,
- hydrogenated diene homopolymers and copolymers,
- linear or branched oligomers, homopolymers or copolymers of alkyl (meth)acrylates preferably containing a $C_8$-$C_{30}$ alkyl group,
- oligomers, homopolymers and copolymers of vinyl esters containing $C_8$-$C_{30}$ alkyl groups,
- oligomers, homopolymers and copolymers of vinyl ethers containing $C_8$-$C_{30}$ alkyl groups,
- liposoluble polyethers resulting from the polyetherification between one or more $C_2$-$C_{100}$ and preferably $C_2$-$C_{50}$ diols,
- esters and polyesters,
- and mixtures thereof.

The pasty fatty substance may be a polymer, especially a hydrocarbon-based polymer.

Among the liposoluble polyethers, mention may be made especially of copolymers of ethylene oxide and/or of propylene oxide with $C_6$-$C_{30}$ alkylene oxides. Preferably, the weight ratio of the ethylene oxide and/or propylene oxide to the alkylene oxides in the copolymer is from 5/95 to 70/30. In this family, mention will be made especially of block copolymers comprising $C_6$-$C_{30}$ alkylene oxide blocks with a molecular weight ranging from 1000 to 10 000, for example a polyoxyethylene/polydodecylene glycol block copolymer such as the ethers of dodecanediol (22 mol) and of polyethylene glycol (45 oxyethylene or OE units) sold under the brand name Elfacos ST9 by Akzo Nobel.

Among the esters, the following are especially preferred:
- esters of a glycerol oligomer, especially diglycerol esters, in particular condensates of adipic acid and of glycerol, for which some of the hydroxyl groups of the glycerols have reacted with a mixture of fatty acids such as stearic acid, capric acid, stearic acid and isostearic acid, and 12-hydroxystearic acid, especially such as those sold under the brand name Softisan 649 by the company Sasol;
- phytosterol esters;
- pentaerythritol esters;
- esters formed from:
  - at least one $C_{16-40}$ alcohol, at least one of the alcohols being a Guerbet alcohol, and
  - from a diacid dimer formed from at least one $C_{18-40}$ unsaturated fatty acid, such as the ester of a dimer of fatty acids and of tall oil comprising 36 carbon atoms and of a mixture i) of Guerbet alcohols comprising 32 carbon atoms and ii) of behenyl alcohol; the ester of a dimer of linoleic acid and of a mixture of two Guerbet alcohols, 2-tetradecyloctadecanol (32 carbon atoms) and 2-hexadecyleicosanol (36 carbon atoms);
- non-crosslinked polyesters resulting from the polycondensation between a linear or branched $C_4$-$C_{50}$ dicarboxylic acid or polycarboxylic acid and a $C_2$-$C_{50}$ diol or polyol,
- polyesters resulting from the esterification between a polycarboxylic acid and an aliphatic hydroxylated carboxylic acid, such as Risocast DA-L and Risocast DA-H sold by the Japanese company Kokyu Alcohol Kogyo, which are esters resulting from the esterification reaction of hydrogenated castor oil with dilinoleic acid or isostearic acid; and
- aliphatic esters of an ester resulting from the esterification between an ester of an aliphatic hydroxycarboxylic acid and an aliphatic carboxylic acid, for example the product sold under the trade name Salacos HCIS (V)-L by the company Nisshin Oil.

A Guerbet alcohol is the reaction product of the Guerbet reaction, which is well known to those skilled in the art. It is a reaction for transforming a primary aliphatic alcohol into its β-alkyl dimeric alcohol with loss of one equivalent of water.

According to a first embodiment, the composition according to the invention is free of pasty fatty substances.

According to a second embodiment, the composition according to the invention comprises at least one pasty fatty substance. The pasty fatty substance(s) may be present in an amount ranging from 0.1% to 40% by weight and especially from 1% to 20% by weight relative to the total weight of the composition.

Pulverulent Phase

A composition according to the invention may comprise a pulverulent phase.

The content of the said pulverulent phase may be between 0.01% and 40% by weight, in particular between 0.1% and 30% by weight and more particularly between 0.1% and 20% by weight relative to the total weight of the composition.

The pulverulent phase may comprise at least one filler and/or at least one colouring agent.

Fillers

The term "fillers" should be understood as meaning colourless or white, mineral or synthetic particles of any shape, which are insoluble in the medium of the composition, irrespective of the temperature at which the composition is manufactured.

The additional fillers may be chosen from fillers such as:

silica microspheres, especially of open porosity or, preferably, hollow silica microspheres, such as the products Silica Beads SB 700/HA or Silica Beads SB 700 from the company Maprecos; these microspheres may be impregnated with a cosmetic active agent;

microporous polymer microspheres, which have a structure similar to that of a sponge; they generally have a specific surface area of at least 0.5 $m^2/g$ and in particular of at least 1 $m^2/g$, the said specific surface area having no upper limit other than that resulting from the practical possibility of making microspheres of very high porosity: the specific surface area may, for example, be up to 1000 $m^2/g$ or even more. Microspheres that may be mentioned include acrylic polymer microspheres, such as those made of crosslinked acrylate copolymer Polytrap 6603 Adsorber from the company RP Scherer, and those made of polymethyl methacrylate Micropearl M 100 from the company SEPPIC;

polyurethane powder, such as the powdered copolymer of hexamethylene diisocyanate and of trimethylol hexyl lactone sold under the names Plastic Powder D-400 and T-7 by the company Toshiki;

polymer microcapsules that comprise a single closed cavity and form a reservoir, which may contain a liquid, especially a cosmetic active agent; they are prepared via known processes such as those described in U.S. Pat. No. 3,615,972 and EP-A-056 219. They may be made, for example, of polymers or copolymers of ethylenically unsaturated acid, amine or ester monomers, of urea-formaldehyde polymers or of vinylidene chloride polymers or copolymers; by way of example, mention may be made of microcapsules made of methyl acrylate or methacrylate polymers or copolymers, or alternatively of copolymers of vinylidene chloride and of acrylonitrile; among these polymers, mention will be made especially of those containing 20-60% by weight of units derived from vinylidene chloride, 20-60% by weight of units derived from acrylonitrile and 0-40% by weight of other units such as units derived from an acrylic and/or styrene monomer; crosslinked acrylic polymers or copolymers may also be used;

elastomeric crosslinked organopolysiloxane spherical powders, described especially in document JP-A-02 243 612, such as those sold under the name Trefil Powder E-506C by the company Dow Corning;

the carnauba wax microbeads sold under the name Microcare 350® by the company Micro Powders and the paraffin wax microbeads sold under the name Microease 114S® by the company Micro Powders;

metal soaps in powder form. Among these soaps, mention may be made especially of metal soaps of fatty acids containing from 12 to 22 carbon atoms and in particular those containing from 12 to 18 carbon atoms. The metal of the metal soap may especially be zinc or magnesium. The fatty acid may be chosen especially from lauric acid, myristic acid, stearic acid and palmitic acid. The metal soaps that may be used include zinc laurate, magnesium stearate, magnesium myristate and zinc stearate, and mixtures thereof;

talcs or hydrated magnesium silicates, especially in the form of particles generally less than 40 µm in size;

micas or aluminosilicates of varied composition that are especially in the form of flakes from 2 to 200 µm and preferably 5-70 µm in size and from 0.1 to 5 µm and preferably 0.2-3 µm in thickness, these micas possibly being of natural origin (for example muscovite, margarite, roscoelite, lepidolite or biotite) or of synthetic origin;

clays such as sericites, which belong to the same chemical and crystalline class as muscovite;

kaolin or hydrated aluminium silicate, which is especially in the form of particles of isotropic forms generally less than 30 µm in size;

boron nitrides;

powders of tetrafluoroethylene polymers, such as Ceridust 9205 F from the company Clariant;

precipitated calcium carbonate, especially in the form of particles greater than 10 µm in size;

magnesium carbonate and magnesium hydrogen carbonate;

hydroxyapatite;

powders of non-expanded synthetic polymers, such as polyethylene, polyesters (for example polyethylene isophthalate or terephthalate) and polyamides (for example Nylon), in the form of particles less than 50 µm in size;

powders of spheronized, crosslinked or non-crosslinked synthetic polymers, for instance polyamide powders such as poly-β-alanine powder or Nylon powder, for example Orgasol powder from the company Atochem, polyacrylic acid or polymethacrylic acid powder, powders of polystyrene crosslinked with divinylbenzene, and silicone resin powders, and bismuth oxychloride powders, powders of organic materials of natural origin, for instance starches, especially corn starch, wheat starch or rice starch;

and mixtures thereof.

A composition according to the invention is advantageously totally free of filler with a refractive index of greater than 1.8.

As representatives of such fillers, mention may especially be made of titanium oxides, zinc oxides and bismuth oxychloride powders.

The additional fillers may be present in the composition in a content ranging from 0.01% to 20% by weight and preferably ranging from 0.1% to 5% by weight relative to the total weight of the composition.

According to one advantageous variant, a composition according to the invention may contain as filler a polyurethane powder and/or mica.

Advantageously, a composition according to the invention may comprise a total content of fillers ranging from 0.01% to 20% by weight, preferably ranging from 0.1% to 10% by weight and preferentially ranging from 0.1% to 5% by weight, relative to the total weight of the composition.

As stated above, a composition according to the invention may also comprise, in its pulverulent phase, at least one colouring agent.

The said at least one colouring agent or dyestuff according to the invention preferably comprises pigments, nacres, reflective particles, colorants that are soluble in polar solvents, and/or mixtures thereof.

According to one particular embodiment, the composition according to the present invention is characterized in that the said at least one colouring agent is present in a content ranging from 0.01% to 10% by weight, in particular from 0.1% to 5% by weight and more preferentially from 0.5% to 2% by weight relative to the total weight of the composition; preferably, the said at least one colouring agent comprises at least one pigment, which is preferentially organic.

Pigments

The term "pigments" should be understood as meaning white or coloured, mineral or organic particles of any form, which are insoluble in the physiological medium and are intended to colour the composition.

The pigments may be white or coloured, and mineral and/or organic.

Among the mineral pigments that may be mentioned are titanium dioxide, optionally surface-treated, zirconium oxide or cerium oxide, and also zinc oxide, iron (black, yellow or red) oxide or chromium oxide, manganese violet, ultramarine blue, chromium hydrate and ferric blue, and metal powders, for instance aluminium powder and copper powder.

The organic pigments may be chosen from the materials below, and mixtures thereof:
cochineal carmine,
organic pigments of azo dyes, anthraquinone dyes, indigoid dyes, xanthene dyes, pyrene dyes, quinoline dyes, triphenylmethane dyes and fluoran dyes.

Among the organic pigments, mention may be made especially of the D&C certified pigments known under the following names: D&C Blue No. 4, D&C Brown No. 1, D&C Green No. 5, D&C Green No. 6, D&C Orange No. 4, D&C Orange No. 5, D&C Orange No. 10, D&C Orange No. 11, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, D&C Violet No. 2, D&C Yellow No. 7, D&C Yellow No. 8, D&C Yellow No. 10, D&C Yellow No. 11, FD&C Blue No. 1, FD&C Green No. 3, FD&C Red No. 40, FD&C Yellow No. 5, FD&C Yellow No. 6.

The chemical materials corresponding to each of the organic dyestuffs mentioned previously are mentioned in the publication "International Cosmetic Ingredient Dictionary and Handbook", 1997 edition, pages 371 to 386 and 524 to 528, published by The Cosmetic, Toiletries and Fragrance Association, the content of which is incorporated into the present patent application by reference.

According to one particular embodiment of the invention, the pigments may be treated or coated with a treatment agent.

The treatment agent may be chosen from alkoxysilanes, silicones such as methicones, dimethicones, and perfluoroalkylsilanes; fatty acids such as stearic acid; metal soaps such as aluminium dimyristate, the aluminium salt of hydrogenated tallow glutamate, perfluoroalkyl phosphates, perfluoroalkylsilanes, perfluoroalkylsilazanes, polyhexafluoropropylene oxides, polyorganosiloxanes comprising perfluoroalkyl perfluoropolyether groups, amino acids, N-acylamino acids or salts thereof; lecithin, isopropyl triisostearyl titanate, and mixtures thereof.

The N-acylamino acids may comprise an acyl group containing from 8 to 22 carbon atoms, for instance a 2-ethylhexanoyl, caproyl, lauroyl, myristoyl, palmitoyl, stearoyl or cocoyl group. The salts of these compounds may be the aluminium, magnesium, calcium, zirconium, zinc, sodium or potassium salts. The amino acid may be, for example, lysine, glutamic acid or alanine According to a preferred variant, a composition according to the invention may comprise a total content of pigments ranging from 0.01% to 70% by weight, preferably ranging from 0.1% to 50% by weight and preferentially ranging from 0.01% to 40% by weight, relative to the total weight of the composition.

When it is a makeup product, a pigment content ranging from 0.01% to 40% by weight, preferably from 0.1% to 30% by weight and in particular from 0.1% to 20% by weight relative to the total weight of the said composition will generally be used.

According to another embodiment variant, a composition according to the invention may be free of pigments.

The pulverulent phase according to the invention may also comprise, or may even be formed from, nacres and/or reflective particles.

The term "nacre" should be understood as meaning coloured particles of any form, which may or may not be iridescent, especially produced by certain molluscs in their shell, or alternatively synthesized, and which have a colour effect via optical interference.

Examples of nacres that may be mentioned include nacreous pigments such as titanium mica coated with an iron oxide, mica coated with bismuth oxychloride, titanium mica coated with chromium oxide, and nacreous pigments based on bismuth oxychloride. They may also be mica particles at the surface of which are superposed at least two successive layers of metal oxides and/or of organic dyestuffs.

The nacres may more particularly have a yellow, pink, red, bronze, orangey, brown, gold and/or coppery colour or glint.

As illustrations of nacres that may be introduced into the composition, mention may be made of the gold-coloured nacres sold especially by the company Engelhard under the name Brilliant gold 212G (Timica), Gold 222C (Cloisonne), Sparkle gold (Timica), Gold 4504 (Chromalite) and Monarch gold 233X (Cloisonne); the bronze nacres sold especially by the company Merck under the name Bronze fine (17384) (Colorona) and Bronze (17353) (Colorona) and by the company Engelhard under the name Super bronze (Cloisonne); the orange nacres sold especially by the company Engelhard under the name Orange 363C (Cloisonne) and Orange MCR 101 (Cosmica) and by the company Merck under the name Passion orange (Colorona) and Matte orange (17449) (Microna); the brown nacres sold especially by the company Engelhard under the name Nu-antique copper 340XB (Cloisonne) and Brown CL4509 (Chromalite); the nacres with a copper tint sold especially by the company Engelhard under the name Copper 340A (Timica); the nacres with a red tint sold especially by the company Merck under the name Sienna fine (17386) (Colorona); the nacres with a yellow tint sold especially by the company Engelhard under the name Yellow (4502) (Chromalite); the red nacres with a gold tint sold especially by the company Engelhard under the name Sunstone G012 (Gemtone); the pink nacres sold especially by the company Engelhard under the name Tan opale G005 (Gemtone); the black nacres with a gold tint sold especially by the company Engelhard under the name Nu antique bronze 240 AB (Timica), the blue nacres sold especially by the company Merck under the name Matte blue (17433) (Microna), the white nacres with a silvery tint sold especially by the company Merck under the name Xirona Silver, and the golden-green pink-orange nacres sold especially by the company Merck under the name Indian summer (Xirona), and mixtures thereof.

Still as examples of nacres, mention may also be made of particles comprising a borosilicate substrate coated with titanium oxide.

Particles having a glass substrate coated with titanium oxide are especially sold under the name Metashine MC1080RY by the company Toyal.

Finally, examples of nacres that may also be mentioned include polyethylene terephthalate flakes, especially those sold by the company Meadowbrook Inventions under the name Silver 1P 0.004×0.004 (silver flakes).

According to one particular variant, the compositions according to the invention may comprise from 0 to 40%, for example 0.1% to 20% and better still 0.5% to 10% by weight of nacres. More preferentially, they contain less than 40% by weight of nacres. According to one particular embodiment, the composition according to the invention is free of nacres.

Finally, the colouring agent according to the invention may comprise reflective particles.

The term "reflective particles" denotes particles whose size, structure, especially the thickness of the layer(s) of which they are made and their physical and chemical nature, and surface state, allow them to reflect incident light. This reflection may, where appropriate, have an intensity sufficient to create at the surface of the composition or of the mixture, when it is applied to the support to be made up, points of overbrightness that are visible to the naked eye, i.e. more luminous points that contrast with their environment by appearing to sparkle.

The reflective particles may be selected so as not to significantly alter the colouration effect generated by the colouring agents with which they are combined, and more particularly so as to optimize this effect in terms of colour yield. They may more particularly have a yellow, pink, red, bronze, orange, brown, gold and/or coppery colour or tint.

These particles may have varied forms and may especially be in platelet or globular form, in particular in spherical form.

The reflective particles, whatever their form, may or may not have a multilayer structure and, in the case of a multilayer structure, may have, for example, at least one layer of uniform thickness, in particular of a reflective material.

When the reflective particles do not have a multilayer structure, they may be composed, for example, of metal oxides, especially titanium or iron oxides obtained synthetically.

When the reflective particles have a multilayer structure, they may comprise, for example, a natural or synthetic substrate, especially a synthetic substrate at least partially coated with at least one layer of a reflective material, especially of at least one metal or metallic material. The substrate may be made of one or more organic and/or inorganic materials.

More particularly, it may be chosen from glasses, ceramics, graphite, metal oxides, aluminas, silicas, silicates, especially aluminosilicates and borosilicates, and synthetic mica, and mixtures thereof, this list not being limiting.

The reflective material may comprise a layer of metal or of a metallic material.

Reflective particles are described especially in documents JP-A-09188830, JP-A-10158450, JP-A-10158541, JP-A-07258460 and JP-A-05017710.

Again as an example of reflective particles comprising a mineral substrate coated with a layer of metal, mention may also be made of particles comprising a silver-coated borosilicate substrate.

Particles with a silver-coated glass substrate, in the form of platelets, are sold under the name Microglass Metashine REFSX 2025 PS by the company Toyal. Particles with a glass substrate coated with nickel/chromium/molybdenum alloy are sold under the name Crystal Star GF 550 and GF 2525 by this same company.

Use may also be made of particles comprising a metallic substrate such as silver, aluminium, iron, chromium, nickel, molybdenum, gold, copper, zinc, tin, manganese, steel, bronze or titanium, the said substrate being coated with at least one layer of at least one metal oxide such as titanium oxide, aluminium oxide, iron oxide, cerium oxide, chromium oxide or silicon oxides, and mixtures thereof.

Examples that may be mentioned include aluminium powder, bronze powder or copper powder coated with $SiO_2$ sold under the name Visionaire by the company Eckart.

Preferably, the pulverulent phase comprises at least one compound chosen from:
organic pigments such as, for example:
the pigments certified D&C by the Food & Drug Administration as listed in the section "Color Additives—Batch Certified by the U.S. Food and Drug Administration" of the CTFA; mention may be made especially of Blue 1 and 4, Brown 1, Ext. Violet 2, Ext. Yellow 7, Green 3, 5, 6 and 8, Orange 4, 5, 10 and 11, Red 4, 6, 7, 17, 21, 22, 27, 28, 30, 36 and 40, Violet 2, Yellow 5, 6, 7, 8, 10 and 11,
mineral pigments such as:
iron oxide, zirconium oxide, cerium oxide, zinc oxide, iron oxide or chromium oxide,
ferric blue, manganese violet, ultramarine blue, pink or violet, chromium hydrate or chromium hydroxide,
nacres such as, for example:
mica coated with titanium oxide, mica coated with titanium oxide and iron oxide, and mica coated with an amino acid such as lauroyl lysine,
polyethylene terephthalate flakes,
sericite,
and mixtures thereof,
reflective particles such as, for example:
particles comprising a borosilicate substrate coated with a metallic layer.

A composition according to the invention may also comprise water-soluble or liposoluble dyes in a content ranging from 0.01% to 10% by weight and especially ranging from 0.01% to 5% by weight relative to the total weight of the composition.

The liposoluble dyes are, for example, Sudan Red, DC Red 17, DC Green 6, β-carotene, soybean oil, Sudan Brown, DC Yellow 11, DC Violet 2, DC Orange 5 and quinoline yellow. The water-soluble dyes are, for example, beetroot juice or methylene blue.

A composition according to the invention may be in the form of a makeup composition product such as a nail varnish, a foundation, a liquid lipstick, a mascara, an anti-wrinkle composition, a skincare composition, or a haircare composition such as a lacquer, a styling lotion or a styling spray.

As hair composition, a composition according to the invention may be used in particular to obtain a hairstyling, hairstyle hold or fixing effect. In particular, the composition may be used for finishing or construction, on dry or wet hair, and optionally with the aid of a heating device.

Among such hair compositions, mention may be made of those for obtaining an improvement in the remanence of compounds inserted into the fibre (for example colorants), or for holding tight on the hair a compound such as photoprotective screening agents or pigments or friction-lowering compounds.

As skincare agent, a composition according to the invention may be used for resistance or beautifying purposes, for treating wounds, or for injecting or antiwrinkle purposes for filling hollow areas of the skin.

A composition according to the invention is more preferentially a nail varnish, the said nail varnish possibly being transparent or coloured.

As nail varnishes, mention may be made of a varnish base or a nailcare product.

A composition according to the invention comprises a physiologically acceptable medium.

The term "physiologically acceptable medium" means a non-toxic medium that may be applied to human keratin materials and that has a pleasant appearance, odour and feel.

Thus, the composition according to the present invention may be applied either by finger or by using a brush or a felt-tip pen. Such a pen is described, for example, in document FR 2 909 844.

EXAMPLES

The examples given below are presented as non-limiting illustrations of the invention.

In the examples that follow, the references of the starting materials used are listed below:

(N-cyclohexylaminomethyl)triethoxysilane: SIC2464.2 (Gelest)

(N-cyclohexylaminomethyl)methyldiethoxysilane: AB152160 (ABCR)

Equimolar mixture of 2,2,4-trimethylhexamethylene diisocyanate and of 2,4,4-trimethylhexamethylene diisocyanate: Vestanat® TMDI (Evonik)

Example 1

Compounds Obtained by Reaction Between 2,2,4-trimethylhexamethylene diisocyanate, 2,4,4-trimethylhexamethylene diisocyanate and (N-cyclohexylaminomethyl)triethoxysilane The synthesis is performed according to the following reaction scheme:

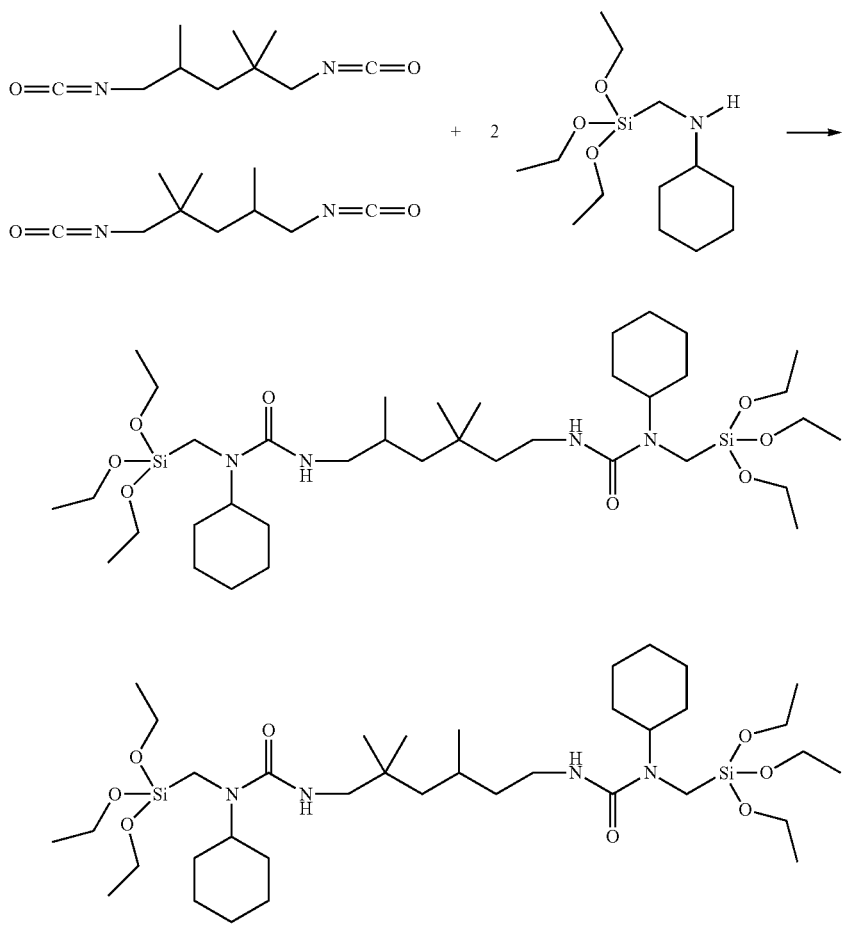

An equimolar mixture of 2,2,4-trimethylhexamethylene diisocyanate and 2,4,4-trimethylhexamethylene diisocyanate (100 g, 476 mmol) is added to (N-cyclohexylaminomethyl)triethoxysilane (262 g, 951 mmol) under nitrogen. The mixture is heated at 65° C. for 3 hours with stirring, under nitrogen. The mixture is then cooled to room temperature.

The compounds obtained are diluted to 50% under nitrogen in ethyl acetate. The solution obtained is applied to a keratin material such as the skin, the nails, the hair or the eyelashes, and forms, after reaction with atmospheric moisture, a strong, adherent film.

Example 2

Compounds Obtained by Reaction Between 2,2,4-trimethylhexamethylene diisocyanate, 2,4,4-trimethylhexamethylene diisocyanate and (N-cyclohexylaminomethyl)methyldiethoxysilane The synthesis is performed according to the following reaction scheme:

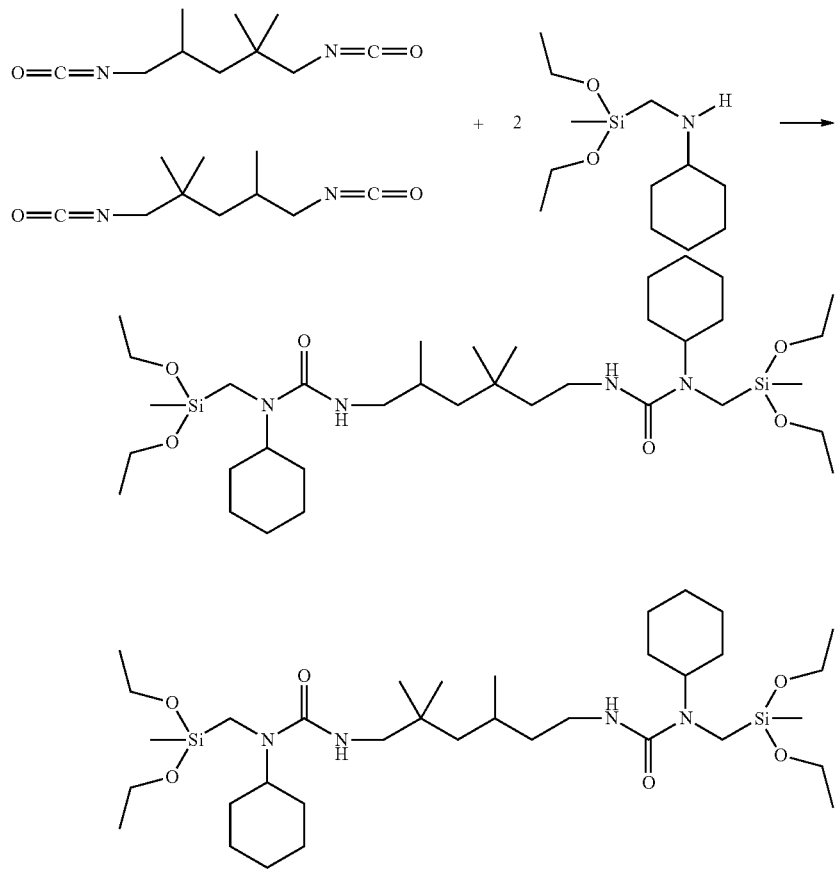

An equimolar mixture of 2,2,4-trimethylhexamethylene diisocyanate and 2,4,4-trimethylhexamethylene diisocyanate (100 g, 476 mmol) is added to (N-cyclohexylaminomethyl)methyldiethoxysilane (232 g, 945 mmol) under nitrogen. The mixture is heated at 65° C. for 3 hours with stirring, under nitrogen. The mixture is then cooled to room temperature.

The compounds obtained are diluted to 50% under nitrogen in ethyl acetate. The solution obtained is applied to a keratin material such as the skin, the nails, the hair or the eyelashes, and forms, after reaction with atmospheric moisture, a strong, adherent film.

The invention claimed is:

1. A cosmetic composition, comprising a compound of formula (I):

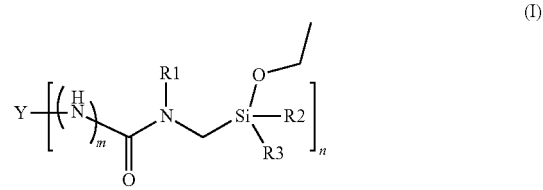

where:

m represents an integer of 0 or 1;

n represents an integer of from 2 to 8;

R1 represents a ($C_1$-$C_{20}$) alkyl group, an aryl group, or optionally a carbonyl group when m is 0;

R2 and R3 represent an ethoxy group or a ($C_1$-$C_{20}$)alkyl group, optionally substituted with an amino group; and Y represents a polyurea, a polyurethane, or a hydrocarbon-based group comprising from 2 to 100 carbon atoms, wherein the hydrocarbon-based group is optionally a linear or branched monovalent or multivalent, optionally unsaturated group, and optionally bears one or more aromatic or non-aromatic cyclic groups,
the carbon atoms are optionally substituted with one or more groups selected from the group consisting of an ethoxy group and an amino group,
one or more of the carbon atoms are optionally independently replaced with
a nitrogen atom,
a carbonyl group,
a —SiO— group, or
a polydimethylsiloxane group:

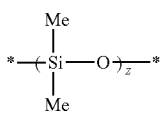

where z is a number of from 1 to 20 and the hydrocarbon-based group optionally forms with R1 one or more rings.

2. The composition according to claim 1, wherein
R1 represents a carbonyl group, and
Y represents
a polyurea;
a polyurethane;
a group chosen from one of the groups of formulae (II) to (XXIII) below when m is 0 or 1; or
a group chosen from one of the groups of chemical formulae (XXIV) to (XXVII) below when m is 0:

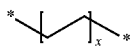

(II)

where:
x is a number of from 1 to 10;
when m is 1, x is 3; and
when m is 0, x is a number of from 2 to 4;

(III)

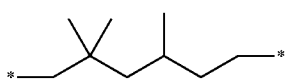

(IV)

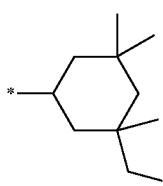

(V)

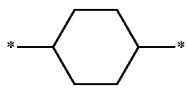

(VI)

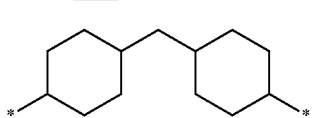

(VII)

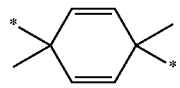

(VIII)

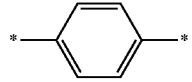

(IX)

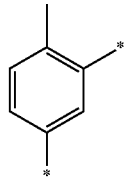

(X)

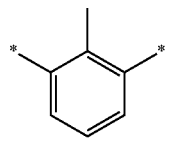

(XI)

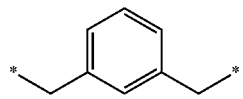

(XII)

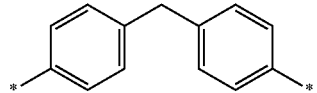

(XIII)

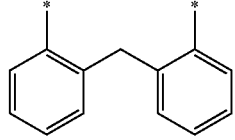

(XIV)

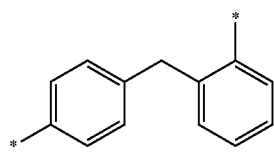

(XV)

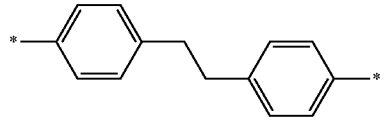

(XVI)

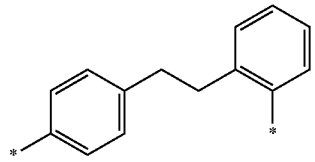

(XVII)

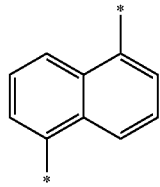

(XVIII)

-continued (XIX)

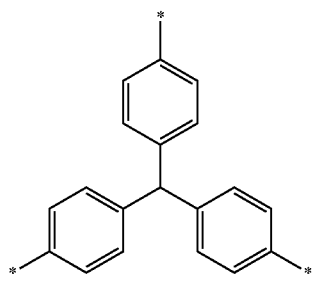

(XX)

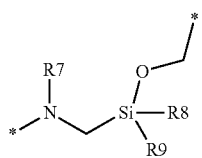

where y is a number of from 1 to 6;

(XXI)

(XXII)

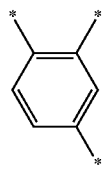

(XXIII)

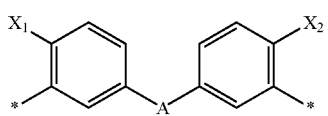

where:
R7 represents a $(C_1\text{-}C_{20})$alkyl group, an aryl group, or a $(C_1\text{-}C_{20})$alkylene group linked to R1; and
R8 and R9 independently represent an ethoxy group or a $(C_1\text{-}C_{20})$alkyl group optionally substituted with an amino group;

(XXIV)

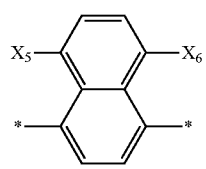

where:
$X_1$ and $X_2$ independently represent a covalent bond linked to R1, which is a carbonyl group; and
A represents a $(C_1\text{-}C_{20})$alkylene group, a carbonyl group or a polydimethylsiloxane of formula (XIX')

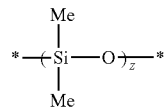

where z is optionally a number of from 1 to 20;

(XXV)

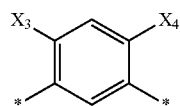

where $X_3$ and $X_4$ independently represent a covalent bond linked to R1, which is a carbonyl group;

(XXVI)

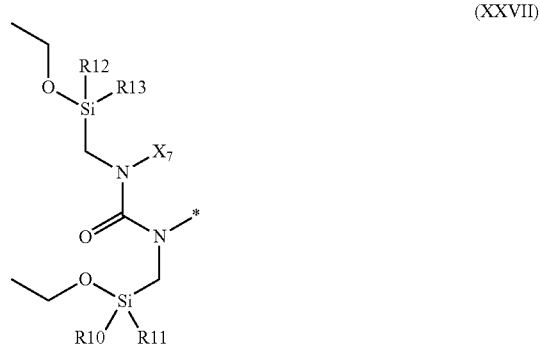

where $X_5$ and $X_6$ independently represent a covalent bond linked to R1, which is a carbonyl group;

(XXVII)

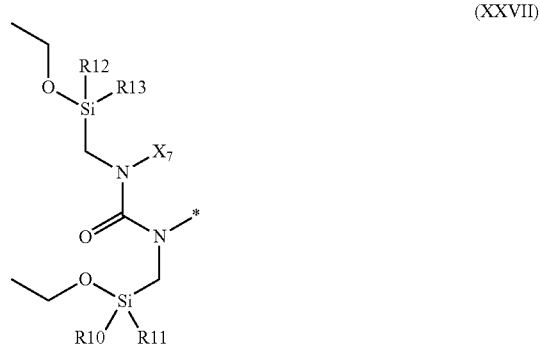

where:
$X_7$ represents a covalent bond linked to R1, which is a carbonyl group; and
R10, R11, R12 and R13 independently represent an ethoxy group or a $(C_1\text{-}C_{20})$alkyl group optionally substituted with an amino group.

3. The composition according to claim 1, wherein Y has a molar mass of less than 3000 g/mol.

4. The composition according to claim 1, wherein n is a number of from 2 to 4.

5. The composition according to claim 1, wherein R1 represents a cyclohexyl or phenyl group.

6. The composition according to claim 1, wherein m is 0 and R1 represents a carbonyl group linked via a covalent bond to one atom of Y.

7. The composition according to claim 1, wherein R2 and R3 independently represent a methyl group, a $(C_1\text{-}C_3)$ aminoalkyl group, or an ethoxy group.

8. The composition according to claim 1, wherein m is 1.

9. The composition according to claim 1, wherein Y is a hydrocarbon-based group consisting of carbon and hydrogen atoms.

10. The composition according to claim 1, wherein Y is a saturated hydrocarbon-based group consisting of carbon and hydrogen atoms.

11. The composition according to claim 2, wherein Y is a group of formula (III), (IV) or (V).

12. The composition according to claim 1, wherein the compound of formula (I) is present in the composition in a content of greater than or equal to 20% by weight relative to a total weight of the composition.

13. The composition according to claim 1, wherein the composition is anhydrous.

14. The composition according to claim 1, wherein the composition has a solids content of greater than or equal to 50%.

15. The composition according to claim 1, further comprising:
- a compound comprising an alkoxysilane group,
- a plasticizer optionally selected from the group consisting of a fatty alcohol, a carboxylic acid ester, and a polyester,
- a film-forming polymer optionally selected from the group consisting of a cellulose derivative, a polyester, and a polyurethane,
- a wax,
- a pasty fatty substance,
- a pulverulent phase comprising a filler and/or a colouring agent comprising pigments, nacres, reflective particles, or colorants that are soluble in polar solvents, and/or a mixture thereof.

16. The composition according to claim 15, wherein the colouring agent is present in a content ranging from 0.01% to 10% by weight relative to a total weight of the composition.

17. The composition according to claim 1, further comprising:
- at least one polar volatile solvent selected from the group consisting of a lower monoalcohol from 1 to 5 carbon atoms, a $C_3$-$C_4$ ketone, a $C_2$-$C_4$ aldehyde, and a $C_2$-$C_4$ short-chain ester.

18. The composition according to claim 1, wherein the composition is optionally a makeup composition.

19. A cosmetic method, comprising:
applying the composition according to claim 1 to a keratin material.

20. The composition according to claim 18, wherein the composition is a nail varnish, a foundation, a liquid lipstick, a mascara, an anti-wrinkle composition, a skin care composition, or a hair care composition.

21. The method according to claim 19, wherein the method is a method for making up nails and/or hair.

* * * * *